United States Patent [19]

Franceschi et al.

[11] Patent Number: 4,507,295

[45] Date of Patent: Mar. 26, 1985

[54] PREPARATION OF AZINOMETHYL-RIFAMYCINS

[75] Inventors: Giovanni Franceschi, Milan; Sergio Vioglio, Cusano Milanino, both of Italy

[73] Assignee: Farmitalia Carlo Erba S.P.A., Milan, Italy

[21] Appl. No.: 590,649

[22] Filed: Mar. 19, 1984

[30] Foreign Application Priority Data

Mar. 24, 1983 [GB] United Kingdom ............... 8308166

[51] Int. Cl.³ .................. C07D 498/08; C07D 521/00
[52] U.S. Cl. ................................................ 260/239.3 P
[58] Field of Search ............... 260/239.3 P; 424/244, 424/267, 274, 248.54, 250, 258

[56] References Cited

U.S. PATENT DOCUMENTS 4,305,941 12/1981 Marsili et al. ............... 260/239.3 P
4,327,096 4/1982 Marsili et al. ............... 260/239.3 P

*Primary Examiner*—Robert T. Bond
*Attorney, Agent, or Firm*—Oblon, Fisher, Spivak, McClelland & Maier

[57] ABSTRACT

Azinomethyl-rifamycins I

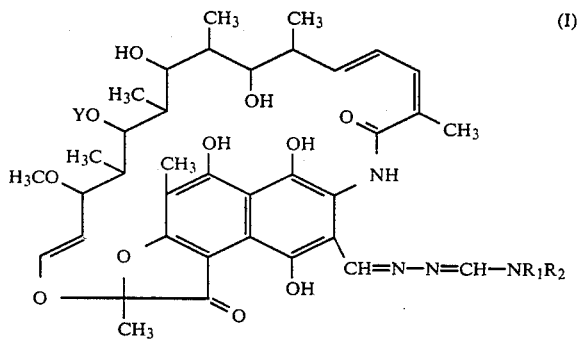

(wherein Y=H or $COCH_3$ and either $R_1=C_1-C_7$ alkyl or $C_3-C_4$ alkenyl and $R_2=C_1-C_7$ alkyl, $C_2-C_4$ cloro-, hydroxy-, or alkoxy-alkyl $C_3-C_4$ alkenyl, cycloalkyl having a $C_3-C_7$ ring, cycloalkylalkyl having a $C_3-C_6$ ring, phenyl or $C_7-C_8$ aralkyl optionally monohalogen substituted in the aryl group or $NR_1R_2=$ a cyclic moiety, said moiety being pyrrolidinyl, piperidinyl, hexahydroazepinyl or heptahydroazocinyl, each of which are unsubstituted or substituted with 1 or 2 methyl radicals, 4-alkyl-1-piperazinyl, morpholinyl or 1,2,3,4-tetrahydroisoquinolinyl) are prepared from rifamycin S by (a) dissolving the rifamycin S in tetrahydrofuran, $CHCl_3$, dioxan, $CH_2Cl_2$ or dichloroethane (b) adding (i) a Schiff's base $CH_2=NR_3$ wherein $R_3=$ t-alkyl or (ii) a compound $R_4N(CH_2OR_5)_2$ wherein $R_4=$ lower alkyl, lower alkenyl, cycloalkyl having a $C_5-C_6$ ring, phenyl, benzyl or α- or β-phenethyl and $R_5=H$ or lower alkyl or (iii) a compound

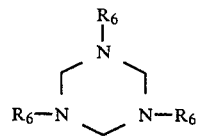

wherein $R_6=C_1-C_6$ alkyl, cycloalkyl having a $C_5-C_6$ ring or alkenyl (c) adding hydrazine and
(d) adding a chloroformiminium chloride

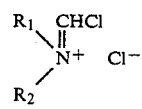

wherein $R_1$ and $R_2$ are as above defined.

6 Claims, No Drawings

PREPARATION OF AZINOMETHYL-RIFAMYCINS

DESCRIPTION

The invention relates to a method for the preparation of azinomethyl-rifamycins having the general formula I

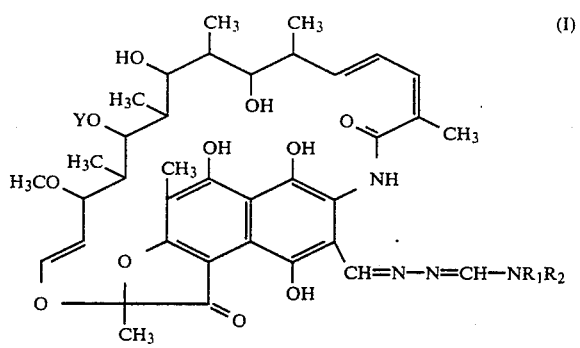

where in Y represents a hydrogen atom or an acetyl group and either $R_1$ represents a linear or branched alkyl group having from 1 to 7 carbon atoms or an alkenyl group having 3 or 4 carbon atoms and $R_2$ represents a linear or branched alkyl group having from 1 to 7 carbon atoms, a cloro- hydroxy- or alkoxy-alkyl having from 2 to 4 carbon atoms, an alkenyl group having 3 or 4 carbon atoms, a cycloalkyl group having from 3 to 7 carbon atoms in the ring, a cycloalkyl-alkyl group having from 3 to 6 carbon atoms in the ring, a phenyl group, an unsubstituted aralkyl group having 7 or 8 carbon atoms or an aralkyl group having 7 or 8 carbon atoms and substituted by one halogen atom in the aryl group, or $R_1$ and $R_2$ together with the nitrogen atom to which they are bonded represent a cyclic moiety, said moiety being pyrrolidinyl, piperidinyl, hexahydroazepinyl or heptahydroazocinyl, each of which are unsubstituted or substituted with 1 or 2 methyl radicals, 4-alkyl-1- piperazinyl, morpholinyl or 1, 2, 3, 4- tetrahydroisoquinolinyl.

These azinomethyl-rifamycins are described and claimed in our British Patent Application No. 8232608. The method described in that Application for their preparation comprises reacting a 3-hydrazonomethyl rifamycin SV having the general formula II

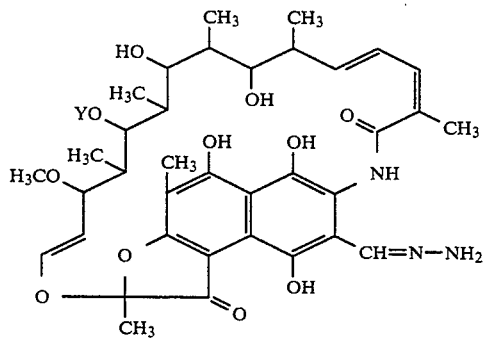

wherein Y represents a hydrogen atom or an acetyl group, in the presence of a tertiary amine and of an aprotic solvent, with a chloroformiminium chloride having the general formula III

wherein $R_1$ and $R_2$ are as above defined. The compounds of the general formula II are disclosed in U.S. Pat. No. 3,342,810.

The method of preparing the compounds of the general formula I consists, therefore, of two separate and well distinguished steps, namely the preparation of compounds of the general formula II and their subsequent reaction with a chloroformiminium chloride of the general formula III in the presence of a tertiary amine. The compounds of the general formula II can be obtained, in accordance with the method described in the aforesaid United States Patent Specification, by reacting 3-formyl rifamycin SV with hydrazine. In its turn, the 3-formyl rifamycin SV is obtained using rifamycin S as starting material and then must be isolated for the reaction with hydrazine: this process is therefore also carried out in two different and separate steps.

The method provided by the invention enables the compounds of the general formula I to be prepared starting directly from rifamycin S and without isolating any intermediate compounds, without using tertiary amines and with the advantageous possibility of crystallizing the azino rifamycins directly from their solvent. The method is therefore quick and simple to effect. The method according to the invention comprises (a) dissolving rifamycin S in tetrahydrofuran, chloroform, dioxan, dichloromethane or dichloroethane, (b) adding to the solution a Schiff's base of the general formula $CH_2=NR_3$ wherein $R_3$ represents tertiary alkyl group, or a compound of the general formula $R_4N(CH_2OR_5)_2$ wherein $R_4$ represents lower alkyl or lower alkenyl group, a cycloalkyl group having 5 or 6 carbon atoms in the ring, or a phenyl, benzyl or α- or β-phenethyl group, and $R_5$ represents a hydrogen atom or a lower alkyl group, or a compound of the general formula

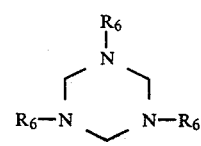

wherein $R_6$ represents an alkyl group having up to 6 carbon atoms, a cycloalkyl group having 5 or 6 carbon atoms in the ring, or an alkenyl group, (c) adding hydrazine to form an intermediate compound which is 3- hydrazonomethyl rifamycin SV having the general formula II as herein defined, and (d) adding to the reaction medium a chloroformiminium chloride having the general formula III as herein defined.

The compounds of formula I thus obtained can be separated from the reaction mixture by crystallization according to the technologies commonly used. It has now been found, that the addition of methyl isobutyl ketone for the crystallization reaction surprisingly gives a highly pure compound in a very good yields.

Preferably, in the method according to the invention, the solvent is tetrahydrofuran, the Schiff's base of formula $CH_2=NR_3$ is obtained from formaldehyde and an alkylamine (preferably t-butylamine) and R₆ represents a t-butyl group.

The following Examples illustrate the invention.

EXAMPLE 1

A solution of N-methylene-t-butylamine (prepared from 3.05 ml of t-butylamine and 0.6 g of paraformaldehyde in tetrahydrofuran) was added to a solution of 6.5 g of rifamycin S in 50 ml of tetrahydrofuran in the presence of 1 g of manganese dioxide, while heating at 50° C. for 3 hours. After filtering off the manganese dioxide, a solution of deep blue colour was obtained. This was cooled to 0° C. and to it was added 0.8 ml of hydrazine hydrate. After 15 minutes (checking the disappearance of the deep blue colour) 5 g of piperidyl chloroformiminium chloride were added portionwise. The mixture was gently warmed to room temperature under stirring and 150 ml of methyl isobutyl ketone was added. The mixture was washed with water and dried on anhydrous sodium sulphate. The solvent was evaporated off until the volume had been reduced to about 50 ml, whereupon 3.2 g of a red compound identified as 3-(piperidylmethylene-azinomethyl)-rifamycin SV (I: $Y=COCH_3$, $NR_1R_2=$piperidyl) crystallized out.

EXAMPLE 2

A solution of 7 g of rifamycin S, 1.7 g of 1,3,5-tri-(t-butyl)-hexahydrotriazine, 0.6 g of paraformaldehyde and 2,4 g of acetic acid in tetrahydrofuran was heated at 50° C. for 1 hour, thus giving a solution of a deep blue colour which was cooled to 5°–10° C. 0.9 ml of hydrazine hydrate were added and the solution was stirred for 15 minutes. 5.5 g of piperidyl chloroformiminium chloride was added portionwise and the mixture was gently warmed to room temperature while stirring for 30 minutes. 170 ml of methyl isobutyl ketone were added, and the resulting solution was washed with water. After drying on anhydrous sodium sulphate, the solvent was evaporated off to a volume of about 70 ml whereupon 3.5 g of a red compound identified as 3-(piperidyl-methylene-azinomethyl)-rifamycin SV (I: $Y=COCH_3$, $NR_1R_2=$piperidyl) crystallized out.

Final compounds similar to those hereabove described can be obtained by using, rather than 1,3,5-tri-tert-butyl hexahydrotriazine, compounds of formula

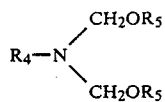

(wherein R₄ is lower alkyl, lower alkenyl, cycloalkyl having 5 or 6 carbon atoms in the ring, phenyl, benzyl, α- or β-phenethyl; and R₅ is hydrogen or an alkyl having a low number of carbon atoms) or of formula

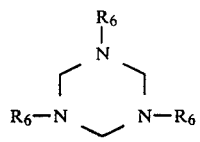

(wherein R₆ is selected from the group consisting of lower alkyl having up to 6 carbon atoms, cycloalkyl having 5 or 6 carbon atoms in the ring, and alkenyl).

We claim:

1. A method for the preparation of an azinomethyl-rifamycin having the formula

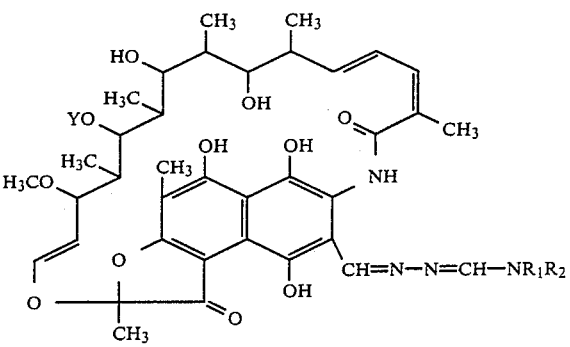

wherein Y represents a hydrogen atom or an acetyl group and either R₁ represents or branched alkyl group having from 1 to 7 carbon atoms or an alkenyl group having 3 or 4 carbon atoms and R₂ represents a linear or branched alkyl group having from 1 to 7 carbon atoms, a chloro-, hydroxy- or alkoxy-alkyl having from 2 to 4 carbon atoms, an alkenyl group having 3 or 4 carbon atoms, a cycloalkyl group having from 3 to 7 carbon atoms in the ring, a cycloalkyl-alkyl group having from 3 to 6 carbon atoms in the ring, a phenyl group, an unsubstituted aralkyl group having 7 or 8 carbon atoms or an aralkyl group having 7 or 8 carbon atoms and substituted by one halogen atom in the aryl group, or R₁ and R₂ together with the nitrogen atom to which they are bonded represent a cyclic moiety, said moiety being pyrrolidinyl, piperidinyl, hexahydroazepinyl or heptahydroazocinyl, each of which are unsubstituted or substituted with 1 or 2 methyl radicals, 4-alkyl-1-piperazinyl, morpholinyl or 1,2,3,4-tetrahydroisoquinolinyl, the method comprising (a) dissolving rifamycin S in tetrahydrofuran, chloroform, dioxan, dichloromethane or dichloroethane,
(b) adding to the solution a Schiff's base of the formula $CH_2=NR_3$ wherein R₃ represents a tertiary lower alkyl group, or a compound of the formula $R_4H(CH_2OR_5)_2$ wherein R₄ represents lower alkyl or lower alkenyl group, a cycloalkyl group having 5 or 6 carbon atoms in the ring, or a phenyl, benzyl or α- or β-phenethyl group, and R₅ represents a hydrogen atom or a lower alkyl group, or a compound of the formula

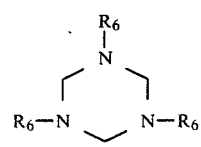

wherein R₆ represents an alkyl group having up to 6 carbon atoms, a cycloalkyl group having 5 or 6 carbon atoms in the ring, or an alkenyl group,
(c) adding hydrazine to form an intermediate compound which is a 3-hydrazonomethyl rifamycin SV having the formula

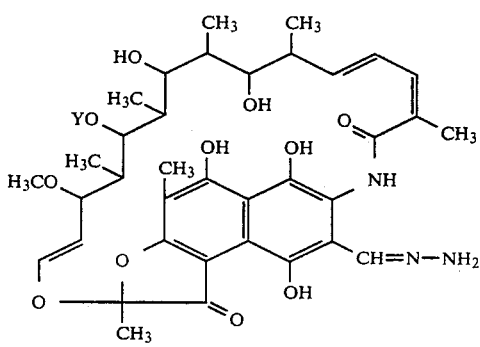

wherein Y represents a hydrogen atom or an acetyl group, and (d) adding to the reaction medium a chloroformiminium chloride having the formula

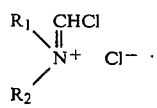

wherein $R_1$ and $R_2$ are as above defined.

2. A method according to claim 1 in which step (b) comprises adding a base obtained from formaldehyde and an alkylamine.

3. A method according to claim 2 in which the alkylamine is t-butylamine.

4. A method according to claim 1 in which step (b) comprises adding 1,3,5-tri-(t-butyl)-hexahydrotriazine.

5. A method according to claim 1 in which the rifamycin S is dissolved in tetrahydrofuran.

6. A method according to claim 1 in which the product is crystallized from the reaction medium by addition of methyl isobutyl ketone.

* * * * *